US007910730B2

(12) United States Patent
Artus Surroca et al.

(10) Patent No.: US 7,910,730 B2
(45) Date of Patent: Mar. 22, 2011

(54) PROCESS FOR THE PREPARATION OF DELMOPINOL AND DERIVATIVES THEREOF

(75) Inventors: Juan Jose Artus Surroca, Vilanova i la Geltrú (ES); David Fernandez Bleda, Castelldefels (ES); Tommaso Iacoangeli, Rome (IT); Jordi Lluis Tous, Tarragona (ES)

(73) Assignee: Sinclair Pharmaceuticals Limited, Surrey (GB)

( * ) Notice: Subject to any disclaimer, the term of this patent is extended or adjusted under 35 U.S.C. 154(b) by 0 days.

(21) Appl. No.: 12/779,288

(22) Filed: May 13, 2010

(65) Prior Publication Data

US 2010/0222579 A1 Sep. 2, 2010

Related U.S. Application Data

(62) Division of application No. 12/092,825, filed as application No. PCT/GB2006/004293 on Nov. 17, 2006.

(30) Foreign Application Priority Data

Nov. 17, 2005 (GB) .................................. 0523435.6

(51) Int. Cl.
*C07D 498/04* (2006.01)
(52) U.S. Cl. ...................................................... 544/105
(58) Field of Classification Search ........................ None
See application file for complete search history.

(56) References Cited

U.S. PATENT DOCUMENTS

| 4,595,751 A | 6/1986 | Blanc |
| 5,155,220 A * | 10/1992 | Hernestam et al. ............ 544/105 |

FOREIGN PATENT DOCUMENTS

| EP | 0 038 785 A1 | 10/1981 |
| WO | WO 90/14342 A | 11/1990 |

OTHER PUBLICATIONS

Mealy N., et al. "Delmopinol hydrochloride. Dental plaque formation inhibitor, treatment of gingivitis" *Drugs of the Future*, Aug. 1996, pp. 787-791, vol. 21, No. 8.
Poerwono H., et al. "Stereocontrolled Preparation of cis- and trans-2,6-Dialkylpiperidines via Diastereoselective Reaction of 1-Aza-4-oxabicyclo[4.3.0] nonane Derivatives with Grignard Reagents" *Tetrahedron*, Nov. 12, 1998, pp. 13955-13970, vol. 54, No. 46.

* cited by examiner

*Primary Examiner* — Kamal A Saeed
*Assistant Examiner* — Nyeemah Grazier
(74) *Attorney, Agent, or Firm* — Saliwanchik, Lloyd & Eisenschenk

(57) ABSTRACT

A process for the preparation of delmopinol (3-(4-propylheptyl)-4-morpholinethanol) or a derivative or a pharmaceutically acceptable salt, or a solvate thereof, including a hydrate, comprises reacting oxazolidin [2,3-c] morpholine and a Grignard reagent, and optionally converting the delmopinol (or derivative) free base into a pharmaceutically acceptable salt. The oxazolidin [2,3-c] morpholine and the Grignard reagent are useful as intermediates in the production process.

1 Claim, No Drawings

PROCESS FOR THE PREPARATION OF DELMOPINOL AND DERIVATIVES THEREOF

This application is a divisional application of co-pending application Ser. No. 12/092,825, filed Aug. 28, 2008; which is a national stage application of International Application Number PCT/GB2006/004293, filed Nov. 17, 2006, which claims priority to Great Britain Application No. 0523435.6, filed Nov. 17, 2005, which are incorporated herein by reference in their entirety.

FIELD OF THE INVENTION

The present invention relates to a process for the production of delmopinol or a derivative thereof, as well as to intermediates useful in the production process.

BACKGROUND TO THE INVENTION

Delmopinol is the International Non-proprietary Name (INN) of 3-(4-propylheptyl)-4-morpholinethanol (CAS No. 79874-76-3). Delmopinol hydrochloride salt (CAS No 98092-92-3) is intended to be used in the treatment of gingivitis. The structure of delmopinol hydrochloride corresponds to formula:

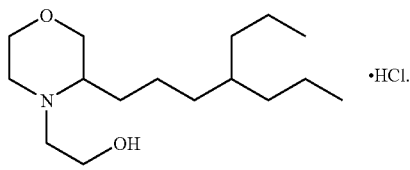

Different processes for the production of delmopinol and its salts are known in the art. EP-A-038785 describes several processes to produce this compound. In particular, EP-A-038785 disclosed the preparation of delmopinol by alkylation of a 3-substituted morpholine, by dialkylation of a primary amine with a substituted bis(haloethyl)ether or a substituted diethyleneglycol disulfonate, by reduction of a diketomorpholine, or by transformation of the N-substituent of the morpholone into a hydroxyethyl group. EP-A-0426826 describes a process for the production of delmopinol which comprises a cycloaddition from a morpholine oxide to obtain a morpholine-iso-oxazolidine, a reductive ring opening, followed by transformation of functional groups present in the side chain, and finally alkylation of the nitrogen to yield delmopinol.

The known processes to produce delmopinol are long and require the use of some very toxic reagents, which make their industrial exploitation difficult and expensive. Therefore, the provision of a new process for producing delmopinol is highly desirable.

SUMMARY OF THE INVENTION

The current invention is based on the surprising realisation that delmopinol, and derivatives thereof, can be obtained by a short and convergent synthesis which takes place through a reaction between an oxazolidin[2,3-c]morpholine compound and a Grignard compound.

According to a first aspect of the present invention, a process for the production of a compound of formula (I) wherein $R_1$ is an alkyl or aryl moiety, or a pharmaceutically acceptable salt, or a solvate thereof, including a hydrate,

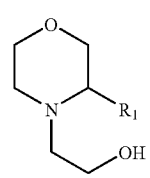 (I)

comprises reacting a compound of formula (II) with a grignard compound of formula (III) where X is an halogen selected from Cl, Br and I and $R_1$ is an alkyl or aryl moiety, and optionally converting the compound of formula (I) free base obtained into a pharmaceutically acceptable salt.

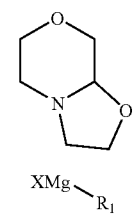 (II)

 (III)

The inventors have also found an efficient production process of the new oxazolidin [2,3-c]morpholine (II), starting from commercially available diethanolamine which proceeds with high yields and purity. Therefore, a second aspect of the present invention is the provision of a process for the production of oxazolidin[2,3-c]morpholine, which involves the reaction of diethanolamine with a $(C_1-C_4)$-alkyl haloacetate yielding the known 4-(2-hydroxyethyl)-morpholin-3-one, followed by a reduction reaction, to yield the oxazolidin[2,3-c]morpholine. Both steps can also be joined in a one pot reaction, avoiding the isolation of the 4-(2-hydroxyethyl)-morpholin-3-one.

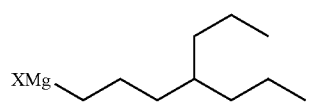 (IIIA)

According to a third aspect of the present invention, the production of a specific grignard compound (IIIA) is carried out by treatment of a 1-halo-4-propylheptane with magnesium.

According to a fourth aspect of the present invention is provided compounds (II) and (IIIA). These are useful as intermediates for the production of a compound of formula (IA).

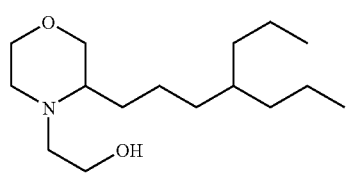 (IA)

According to a fifth aspect of the invention, compounds (II) and (III) are used in the manufacture of a compound of formula (I).

The process of the present invention is an easy and efficient alternative to manufacture delmopinol, derivatives of delmopinol and/or pharmaceutically acceptable salts thereof, on an industrial scale. The process is advantageous because it is a short and convergent synthesis, it avoids the use of toxic and flammable reagents, it uses mild reaction conditions, and delmopinol is obtained with high yields and high purity.

DETAILED DESCRIPTION OF THE INVENTION

A compound of formula (I) is produced according to the present invention.

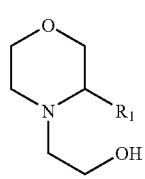
(I)

In the compound of formula (I), $R_1$ is an alkyl or aryl moiety. The alkyl or aryl moiety can be of any length, can be straight-chain or branched and can be substituted, i.e. can contain atoms other than carbon in the carbon backbone. As used herein, the terms "alkyl" and "aryl" are to be given their usual meanings on the art. Preferably, the alkyl or aryl moiety comprises between 1 and 30 carbon atoms, more preferably between 2 and 20 carbon atoms, for example 6,7,8,9 or 10 carbon atoms. Compounds of formula (I) have been prepared where the $R_1$ group is a 1-Propyl, Benzyl, 1-Octyl, 1-Heptyl, 1-(2-ethyl)hexyl or 1-(2-propyl)hexyl group. The preparation of these compounds is described in Examples 6 to 11.

A preferred compound of formula (I) is delmopinol, which is represented below as formula (IA). In delmopinol, $R_1$ is a 4-propylheptyl chain.

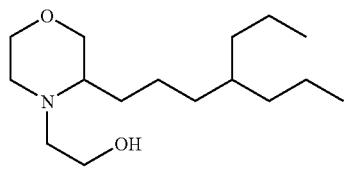
(IA)

According to the present invention, a compound of formula (I) is obtained by a reaction between the oxazolidin[2,3-c]morpholine (II) and the Grignard compound (III) where X is an halogen selected from Cl, Br and I, and $R_1$ is an alkyl or aryl moiety as defined above and most preferably a 4-propylheptyl chain. A preferred compound of formula (III), wherein $R_1$ is a 4-propylheptyl chain is depicted as formula (IIIA) below.

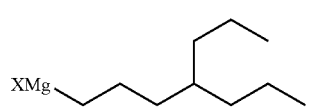
(IIIA)

Most preferably, the compound of formula (III) is 4-propylheptylmagnesium bromide. As used herein, the term "Grignard Compound" is to be given its standard meaning, which is well known in the art, i.e. an organo-magnesium compound.

For the avoidance of doubt, a compound of formula (I) is prepared by reacting a compound of formula (II) with a Grignard compound of formula (III). A preferred embodiment of this general reaction comprises the production of delmopinol (formula (IIIA) by reacting a compound of formula (II) with the preferred Grignard compound of formula (IIIA).

The formation of the Grignard compound (III) and its subsequent reaction with the oxazolidine (II) is carried out in a suitable solvent such as ethers ($C_4$-$C_{12}$) and mixtures of said ethers with ($C_5$-$C_8$) aliphatic or ($C_6$-$C_8$) aromatic hydrocarbons. Preferably the solvent is selected from the group consisting of diethylether, tetrahydrofuran, methyltetrahydrofuran, dibutylether and the following mixtures: tetrahydrofuran-toluene, tetrahydrofuran-xylene, methyltetrahydrofuran-toluene, methyltetrahydrofuran-xylene, dibutylether-xylene, dibutylether-toluene.

A compound of formula (I), for example delmopinol, obtained by the process of the present invention may be converted into a pharmaceutically acceptable salt, preferably into the hydrochloride salt, and delmopinol salts may be converted into delmopinol, by known methods described in the art. By a way of example, delmopinol hydrochloride can be prepared from delmopinol by reaction with hydrochloric acid in any suitable solvent. Examples of suitable solvents are, for instance, toluene, xylene, methylisobutylketone, dibutylether, methyl-tert-butylether, ethyl acetate, and mixtures thereof.

The compound of formula (II) can be obtained by the process summarised in Scheme I, which can be carried out in two steps or as a one pot reaction. As used herein, the term "one pot reaction" is to be given its normal meaning in the art, i.e. the compound of formula (II) is produced in a single reaction vessel, such that at least a proportion of compounds (V) and (VI) are converted to compound (IV), and subsequently compound (II), without the isolation of intermediates.

The alternative to a one pot reaction is a two step reaction wherein formula (IV) is produced in a first step, and the second step of converting (IV) into (II) is carried out separately.

SCHEME I:

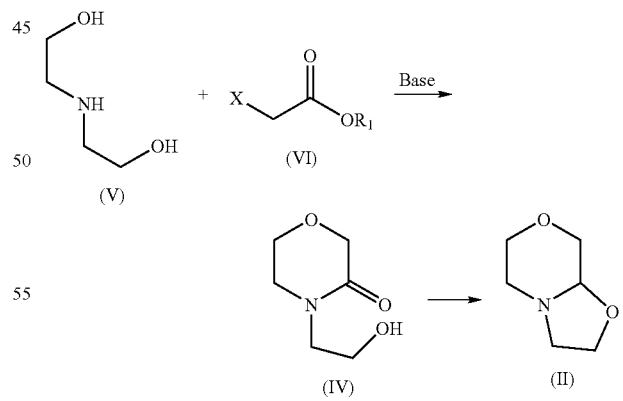

In formula (VI). X is an halogen selected from Cl, Br and I, and $R_1$ is a ($C_1$-$C_4$)-alkyl radical. Preferably the compound of formula (VI) is methyl chloroacetate.

The reaction between the diethanolamine (V) and the haloacetate of formula (VI) is preferably carried out in the presence of a suitable base and a suitable solvent. Examples of suitable bases are sodium hydride, sodium methoxide, potassium tert-butoxyde and sodium tert-butoxide. The best results are obtained with potassium tert-butoxide. Suitable solvents are for example tetrahydrofuran, xylene, toluene or dibutylether.

The reaction between the diethanolamine (V) and the haloacetate (VI) can be carried out at a temperature between room temperature and the reflux temperature of the solvent used. Preferably, the reaction is carried out at high temperatures (i.e. slightly less than the reflux temperature of the solvent, for example 50% of the reflux temperature or above, preferably 60%, 70%, 80% or 90% of the reflux temperature) to avoid thickness of the crude mixture by insolubility of diethanolamine alkoxyde at low temperatures. Compound (IV) can be isolated from the reaction medium with high yield as an oil, which can be used without purification in the next step. If required, it can be purified by distillation.

3-Morpholinone (IV) can also be prepared by a process described in the literature (Australian Journal of Chemistry, 1996, vol. 49, pp. 1235-1242). However, this process uses an excess of acylating reagent, it goes through an unstable intermediate and proceeds with low yields.

The reduction of 3-morpholinone (IV) to yield the oxazolidine (II) is carried out using a reducing agent. Examples of reducing agents are sodium bis(2-methoxyethoxy)aluminum hydride (Vitride), sodium borohydride, lithium aluminium hydride and sodium bisethoxyaluminum hydride. A preferred reducing agent is sodium bis(2-methoxyethoxy)aluminum hydride. The reduction reaction is carried out in a solvent selected from a ($C_6$-$C_8$) aromatic hydrocarbon such as toluene or xylene and an ether ($C_4$-$C_{12}$) such as diethylether, tetrahydrofuran, dibutylether, methyl tert-butylether, and diethyleneglycol dibutyl ether.

Preferably, when the process of producing the compound of formula II is carried out in one pot, the alcohols generated during the reaction between the diethanolamine and the compound of formula (VI) are distilled before adding the reducing agent.

The compound of formula (III) can be produced by reacting an alkyl or aryl halide with magnesium. Preferably, the halide is in the terminal or secondary position. In a preferred embodiment, as illustrated in Scheme II, the compound of formula (IIIA) is previously prepared by treating a compound of formula (VII) wherein X is an halogen selected from Cl, Br, and I, with magnesium. Any suitable solvent for Grignard reactions such as ethers ($C_4$-$C_{12}$) and mixtures of such ethers with ($C_5$-$C_8$) aliphatic or ($C_6$-$C_8$) aromatic hydrocarbons can be used for the formation of Grignard compound. The Grignard compound of formula (III) is not isolated and is used in solution. Its formation is easily detectable by the disappearance of magnesium and the brownish colouration of the solution.

SCHEME II:

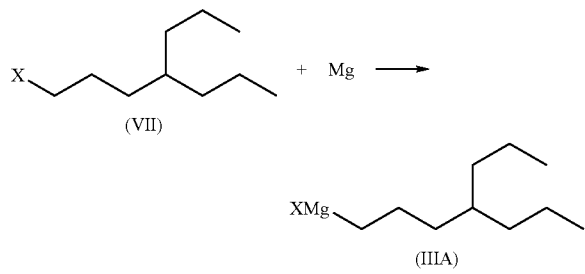

The compound of formula (VII) can be prepared from the corresponding hydroxy compound of formula (VIII) by an halogenation reaction.

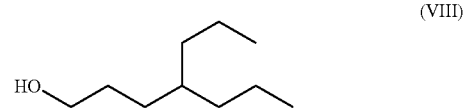

Preferably in the compound of formula (VII), X is bromine and is preferably obtained by a brominating reaction of the compound (VIII) with aqueous hydrobromic acid. The compound of formula (VIII) can be prepared by the process described in Justus Liebigs Annalen Chemie, 1966, vol. 693, p. 90, the content of which is hereby incorporated by reference.

Throughout the description and claims the word "comprise" and variations of the word, such as "comprising", are not intended to exclude other technical features, additives, components, or steps. Additional objects, advantages and features of the invention will become apparent to those skilled in the art upon examination of the description or may be learned by practice of the invention.

The following examples are provided by way of illustration, and are not intended to be limiting of the present invention.

EXAMPLES

Example 1

Production of 4-(2-hydroxyethyl)morpholin-3-one (IV)

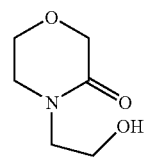

Potassium tert-butoxyde (176 g, 1.1 eq.) was added to 1440 ml of toluene. The suspension was heated to 75° C. and maintained for 30 minutes until complete dissolution of the white solid. At this temperature diethanolamine (150 g, 1 eq.) was slowly added. The thick pale yellow suspension was maintained with strong stirring for 30 minutes and methyl chloroacetate (163 g, 1.05 eq.) was added slowly. The solution was maintained at the same temperature for two hours. To the warm mixture methanol (600 ml) was added and cooled at room temperature, salts were filtrated and the organic layer concentrated until dry. Compound (IV) was obtained as an orange oil (204 g, 98%) which was distilled under high vacuum to obtain it as a highly pure colorless oil (80%, bp5 180° C.). IR (film) (n cm−1): 3410, 2934, 2874, 1633, 1501, 1350, 1141. MS (EI), (m/z, %): 145 (M+., 12), 114 (M-CH2OH, 100), 86 (M-NC2H4OH, 65), 74 (M-71, 7), 56 (M-89, 41), 42 (M-103, 44).

Example 2

Production of oxazolidin[2,3-c]morpholine (II)

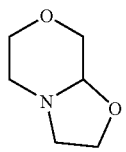

To a solution of 3-morpholinone (IV) (207 g, 1 eq.) in toluene (1450 ml), Vitride solution (412 g, 2 eq., 70% in toluene) was slowly added at room temperature. The reaction was maintained for 15 min at this temperature. 50% aqueous sodium hydroxide solution (360 g, 3.15 eq.) was slowly added keeping the mixture at room temperature. The mixture was warmed to 50-60° C. and the aqueous layer was separated and extracted at the same temperature with toluene (924 ml). Both organic layers were concentrated together until dry. Oxazolidine (II) was obtained (154.5 g, 84%) as a brownish oil, which was distilled to give a highly pure colorless oil (65 g, bp2 80° C.). IR (film), (n cm−1): 2865, 1676, 1457, 1297, 1113, 1046. MS (EI), (m/z, %): 129 (M+., 50), 99 (M-CH2O, 100), 98 (M-CH3O, 90), 84 (M-C2H5O, 10), 71 (M-C3H6O, 51), 56 (M-73, 37), 42 (M-87, 47), 41 (M-88, 65).

Example 3

Production of oxazolidin[2,3-c]morpholine (II) in a one-pot reaction starting from diethanolamine Potassium tert-butoxyde (176 g, 1.1 eq.) was added to 1440 ml of toluene. The suspension was heated to 75° C. and maintained for 30 min. until complete dissolution of the white solid. At this temperature diethanolamine (150 g, 1 eq.) was added slowly. The thick pale yellow suspension was maintained with strong stirring for 30 min. and methyl chloroacetate (163 g, 1.05 eq.) was added slowly. The solution was maintained at the same temperature for two hours. Reaction mixture was cooled at 30° C. and Vitride solution (412 g, 2 eq., 70% in toluene) was added slowly at room temperature. The reaction was maintained for 30 min at this temperature. 50% aqueous sodium hydroxide solution (360 g, 3.15 eq.) was added slowly keeping the mixture at room temperature. The mixture was warmed to 50° C. and the aqueous layer was separated and extracted at the same temperature with toluene (924 ml). Both organic layers were concentrated together until dry. Oxazolidine (II) was obtained (147 g, 80%) as a brownish oil.

Example 4

Production of 4-(2-hydroxyethyl)-3-(4-propylheptyl)morpholine (IA)

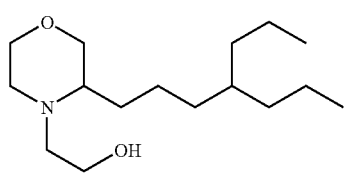

To a suspension of 1.3 g of magnesium (1 eq.) in 24 ml of toluene and 18 ml of tetrahydrofuran a small crystal of iodine was added. The mixture was heated at 64° C. and 12 g of 1-bromo-4-propylheptane (VII) (1 eq.) was added slowly controlling exothermicity of the reaction. The mixture was maintained at the same temperature for 2 hours and cooled at room temperature, obtaining a solution of compound (III). A solution of 7 g of oxazolidine (II) (1 eq.) in 7 ml of toluene was added to the previously prepared Grignard compound (III) at room temperature in 30 min. 50 ml of toluene and 50 ml of saturated aqueous ammonium chloride solution were added and the resulting mixture was stirred at 40° C. until complete dissolution of salts, obtaining a biphasic mixture. The organic layer was separated at 40° C. The aqueous layer was extracted with 50 ml of toluene at 40° C. Organic layers were concentrated together till dry, obtaining 8.8 g of 4-(2-hydroxyethyl)-3-(4-propylheptyl)morpholine as an orange oil. IR (film), (n cm−1): 3446, 2951, 2925, 2859, 1628, 1458, 1128, 1048. MS (EI), (m/z, %): 271 (M+., 1), 270 (M-H, 1), 240 (M-CH2OH, 46), 130 (M-141, 100), 100 (M-171, 29).

Example 5

Production of 4-(2-hydroxyethyl)-3-(4-propylheptyl)morpholine Hydrochloride

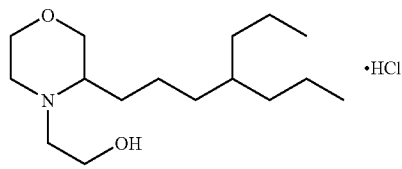

To a solution of 7.4 g of crude 4-(2-hydroxyethyl)-3-(4-propylheptyl)morpholine in 22 ml of methyl iso-butyl ketone at room temperature concentrated hydrochloric acid (2.7 g, 1 eq.) was added. The solution was concentrated until dry at 60° C. The oil was dissolved again in 21 ml of methyl iso-butyl ketone the solution was seeded and stirred for 2 hours at 0° C. The white solid was filtered, washed with 20 ml of cold methyl iso-butyl ketone and dried to obtain 5.9 g of 4-(2-hydroxyethyl)-3-(4-propylheptyl)morpholine hydrochloride (delmopinol hydrochloride). 1H-NMR (CDCl3, 400 MHz), (d ppm): 0.88 (6H, m, H15), 1.2-1.4 (13H, m), 1.8-2.0 (2H, m), 2.8-3.4 (5H, m), 3.4-4.4 (6H, m). 13C-NMR (CDCl3, 400 MHz), (d ppm): 14.26 (015), 19.47, 19.52 (C14), 22.87 (C10), 27.11 (C9), 33.25 (C11), 35.54, 35.62 (C13), 36.59 (C12), 49.25 (C5), 53.20 (C7), 55.93 (C3), 57.08, 59.89 (C8), 63.1, 63.2, 65.0 (C6), 67.7 (C2).

Example 6

Synthesis of 4-(2-Hydroxyethyl)-3-propylmorpholine (IB)

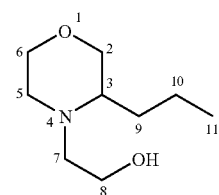

43 g of Oxazolidine(II) was dissolved in 215 ml of THF. At room temperature a solution of n-Propylmagnesiumchloride 20% in THF (172 g, 1 eq) was slowly added. The mixture was stirred for 15 minutes. Mixture was concentrated until dryness under vacuum and 100 ml of Toluene and 64 g of saturated aqueous Ammonium Chloride solution were added and the resulting mixture was stirred at room temperature until complete dissolution of salts obtaining a biphasic mixture. Organic layer was separated and aqueous layer was extracted with 265 ml of Toluene at room temperature. Organic layers were concentrated together until dryness, obtaining 33.4 g of 4-(2-Hydroxyethyl)-3-propylmorpholine like a orange oil, which was further purified by column chromatography in silica gel eluting with a mixture of CH2Cl2/MeOH/NH3 (99/1/1), obtaining the mentioned product as a colorless oil. 1H-NMR (CDCl3, 300 MHz), (d ppm): 0.92 (3H, t, J=7.2 Hz, H11), 1.36 (4H, m, H9/H10), 2.36 (3H, m, H3/H7), 2.82 (1H, ddd, J1=12.3, J2=4.9, J3=3.0 Hz, H5), 2.94 (1H, ddd, J1=12.3, J2=7.8, J3=4.8 Hz, H5), 3.44 (1H, dd, J1=11.2, J2=6.9 Hz, H2), 3.88 (1H, dd, J1=4.9 Hz, H2), 3.62 (1H, dd, J1=4.8, J2=7.8 Hz, H6), 3.67 (1H, dd, J1=7.8, J2=4.9 Hz, H6), 3.75 (2H, m, H8). 13C-NMR (CDCl3, 75 MHz), (d ppm): 14.3 (C11), 19.3 (C10), 29.2 (C9), 49.9 (C5), 54.6 (C7), 57.7 (C8), 59.5 (C3), 66.9 (C6), 70.4 (C2). IR (film), (n cm−1): 3444, 2958, 2863, 1456, 1366, 1129, 1052. MS (EI), (m/z, %): 173 (M+., 42), 142 (M-CH2OH, 100), 130 (M-C3H7, 100), 112 (M-C3H7-H2O, 14), 100 (M-73, 48), 84 (10), 71 (5), 56 (20), 42 (14).

Example 7 of 4-(2-Hydroxyethyl)-3-(1-heptyl)morpholine(IC)

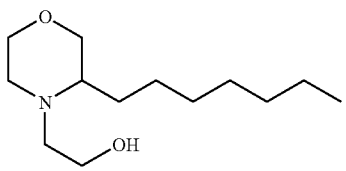

200 g of 1-Bromoheptane were slowly added at 65° C. to a suspension of 32.6 g of magnesium, 0.5 g of iodine and 2.4 ml of Dibromoetane in a mixture of 182 ml of THF and 400 ml of toluene. The reaction mixture was stirred at the same temperature for 3 h. When the formation of the corresponding Grignard compound was completed, the mixture was cooled down at room temperature and a solution of 158 g of Oxazolidine (II) in 500 ml of toluene was added in 1 hour. The mixture was stirred for 30 min. and then added to 795 ml solution of aqueous 5% HCl. The organic layer is decanted and concentrated until dryness. Compound (IC) was obtained as an orange oil (179 g). MS (EI), (m/z, %): 229 (M+., 1), 198 (M-CH2OH, 25), 130 (M-C7H15, 100), 112 (M-C7H15-H2O, 4), 100 (M-73, 30), 86 (5 56 (10), 41 (8).

Example 8

Synthesis of 4-(2-Hydroxyethyl)-3-benzylmorpholine(ID)

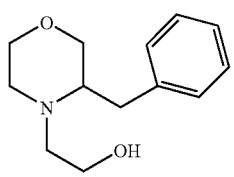

Following the same procedure described for (IC) and starting from 10 g of Benzyl chloride and 11 g of Oxazolidine (II), 7.9 g of compound (ID) was obtained as an light yellow oil. MS (EI), (m/z, %): 221 (M+., 1), 190 (M-CH2OH, 5), 130 (M-C7H7, 100), 91 (CH2C6H5, 8)

Example 9

Synthesis of 4-(2-Hydroxyethyl)-3-(1-octyl)morpholine(IE)

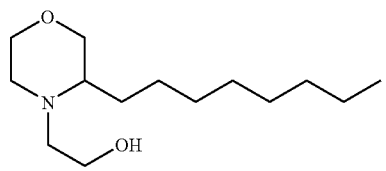

25 g of 1-Bromooctane were slowly added to a suspension of 3.5 g of magnesium and 7.5 mg of iodine in 41 ml of THF at 65° C. The reaction mixture was stirred at the same temperature for 2 h. When the corresponding Grignard compound was prepared, the mixture was cooled down at 5° C. and a solution of 16.7 g of Oxazolidine (II) in 40 ml of toluene was added in 1 hour. The mixture was stirred at 5° C. for 30 min. and the reaction was warmed up until room temperature. The mixture was added to an aqueous solution of 5% HCl and stirred for 30 min. The organic layer was decanted, dried and concentrated until dryness to obtain 19 g of the desired compound as a brown oil. MS (EI), (m/z, %): 243 (M+., 5), 242 (M-H, 5), 212 (M-CH2OH, 50), 198 (M-(CH2) 2OH, 8), 130 (M-C8H17, 100), 112 (M-C8H17-H2O, 8), 100 (M-73, 30), 86 (8), 71 (8), 56 (9), 41 (14).

Example 10

Synthesis of 4-(2-Hydroxyethyl)-3-(1-(2-ethylhexyl))morpholine(IF)

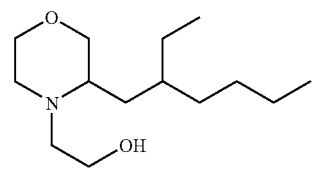

Following the same procedure described for (IE) and starting from 25.5 g g of 1-Bromo-2-ethylhexane bromide and 16.2 g of Oxazolidine (II), 19.8 g compound (IF) were obtained as an dark orange oil. MS (EI), (m/z, %): 243 (M+., 1), 214 (M-C2H5, 6), 212 (M-CH2OH, 11), 186 (M-C4H9, 4), 156 (8), 130 (M-C8H17, 100), 100 (46).

Example 11
Synthesis of 4-(2-Hydroxyethyl)-3-(1-(2-propylpentyl))morpholine(IG)
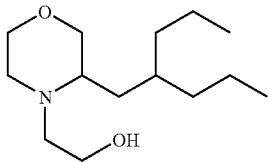
Following the same procedure described for (IE) and starting from 5.8 g g of 1-Bromo-2-propylpentane and 4 g of Oxazolidine (II), 3.3 g of compound (IF) were obtained as an dark yellow oil. MS (EI), (m/z, %): 243 (M+., 1), 212 (M-CH2OH, 8), 200 (M-C3H7, 6), 170 (10), 130 (M-C8H17, 100), 100 (50).
We claim:
1. A compound of formula (II)
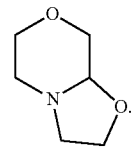
(II)
* * * * *